US006184394B1

(12) United States Patent
Falling

(10) Patent No.: US 6,184,394 B1
(45) Date of Patent: Feb. 6, 2001

(54) PROCESS FOR THE PREPARATION OF 3-FUROATE ESTERS AND NOVEL INTERMEDIATE COMPOUNDS

(75) Inventor: Stephen Neal Falling, Kingsport, TN (US)

(73) Assignee: Eastman Chemical Company, Kingsport, TN (US)

( * ) Notice: Under 35 U.S.C. 154(b), the term of this patent shall be extended for 0 days.

(21) Appl. No.: 09/491,654

(22) Filed: Jan. 27, 2000

(51) Int. Cl.[7] .................... C07D 307/20; C07D 307/68
(52) U.S. Cl. ............................ 549/475; 549/486
(58) Field of Search .................... 549/475, 486

(56) References Cited

U.S. PATENT DOCUMENTS 5,259,701  11/1993  Gerhart et al. .

OTHER PUBLICATIONS

S. P. Tanis, Tetrahedron Letters, vol. 23, No. 31, pp. 3115–3118 (1982).
T. Reichstein et al., Helv. Chim. Acta, 15, pp. 268–273 (1932).
T. Reichstein et al., Helv. Chim. Acta, 16, pp. 276–281, (1933).
D. Dare et al., J. Chem. Soc., Perkin I, pp. 1130–1134 (1973).
M. Boyd et al., Synthesis, pp. 545–546 (1971).
L. W. Deady et al., Synthesis, p. 571 (1972).
E. Sherman et al., J. Am. Chem. Soc., 72, pp. 2195–2199 (1950).
Gilman et al., J. Am. Chem. Soc., 55, pp. 2903–2909 (1933).
Y. Fukuyama et al., Synthesis, pp. 443–444 (1974).
I. Fleming et al., Synthesis, p. 898 (1985).
O. Sock et al., Tetrahedron Letters, vol. 26, No. 12, pp. 1509–1512 (1985).
E. Wenkert et al., J. Organic Chem., 55, pp. 4975–4976 (1990).
S. R. Olsen et al., J. Chem. Soc. (C), pp. 1632–1633 (1971).
G. Ya. Kondrat'eva et al., Proc. of the Academy of Sciences, USSR (Chem.), 200, pp. 862–864 (1971).
E. Baciocchi et al., Synthetic Communications, 18 (15), pp. 1841–1846 (1988).
F. Effenberger et al., Chem. Ber., 115, pp. 2766–2782 (1982).
M. Hojo et al., Synthesis, pp. 1016–1017 (1986).
M. Hojo et al., Chemistry Letters, pp. 499–502 (1976).
N. Zanatta et al., J. Heterocyclic Chem., 34, pp. 509–513 (1997).
P. Maynard–Faure et al., Tetrahedron Letters, 39, pp. 2315–2318 (1998).
J. T. Wrobel et al., Rocz. Chem., 40, pp. 1005–1018 (1966).
W. Hasenbrink, Liebigs Ann. Chem., pp. 468–476 (1974).
D. H. Williams et al., Tetrahedron, vol. 52, No. 12, pp. 4245–4256 (1996).
R. C. Fuson, et al., Chem. Rev., vol. 15, No. 3, pp. 275–309 (1934).

*Primary Examiner*—Joseph K. McKane
*Assistant Examiner*—Andrea D'Souza
(74) *Attorney, Agent, or Firm*—Michael J. Blake; Harry J. Gwinnell

(57) ABSTRACT

Disclosed is a two-step process wherein a 4-acyl-2,3-dihydrofuran is converted to a 2-alkoxy-3-acyl-3-halotetrahydorfuran which then is contacted with an strong base to produce an alkyl 3-furoate. Also disclosed are novel 2-alkoxy-3-acyl-3-halotetrahydrofuran intermediates.

13 Claims, No Drawings

PROCESS FOR THE PREPARATION OF 3-FUROATE ESTERS AND NOVEL INTERMEDIATE COMPOUNDS

BACKGROUND OF THE INVENTION

This invention pertains to the preparation of 3-furoate esters and to certain novel intermediate compounds. More particularly, this invention pertains to a two-step process wherein a 4-acyl-2,3-dihydrofuran is converted to a 2-alkoxy-3-acyl-3-halotetrahydrofuran which then is contacted with an alkoxide to produce an alkyl 3-furoate. The 2-alkoxy-3-acyl-3-halotetrahydrofuran intermediates are novel compounds.

Unlike 2-furoic acid and its esters which are derived from inexpensive furfural, 3-furoic acid and its esters have been, in the past, difficult and expensive to synthesize in any amount. Preparation of 3-substituted furans from furan itself requires multiple steps because the 2-position of furan is more activated toward aromatic substitution reactions. Although several literature references describe methods to produce 3-substituted furans, many contain comments on the difficulty of synthesizing such compounds. For example, S. P. Tanis states in *Tetrahedron Letters*, 23, 3115–3118 (1982): "Although many methods have been reported for the synthesis of 3-substituted furans they generally require many steps, relatively inaccessible starting materials, or proceed in low overall yields."

Most literature processes for the preparation of 3-furoic acid or ester involve the decarboxylation of furandicarboxylic acids. T. Reichstein, et al., *Helv. Chim. Acta*, 15, 268–273 (1932); 16, 276–281 (1933), reported the preparation of 3-furoic acid from either furan-2,3-dicarboxylic acid, furan-3,4-dicarboxylic acid or furan-2,4-dicarboxylic acid. These dicarboxylic acids are obtained in low yield via several intermediate steps. See also D. Dare, et al., *J. Chem. Soc., Perkin I*, 1130–1134 (1973); M. Boyd, et al., *Synthesis*, 545–546 (1971); L. W. Deady, et al., *Synthesis*, 571 (1972). In a simplification of Reichstein's process, E. Sherman, et al. decarboxylated furantetracarboxylic acid to give 3-furoic acid (*J. Am. Chem. Soc.*, 72, 2195–2199 (1950)). Gilman, et al., *J. Am. Chem. Soc.*, 55, 2903–2909 (1933) reported the decarboxylation of 2,4-furandicarboxylic acid to 3-furoic acid which was converted to ethyl 3-furoate via 3-furoyl chloride.

3-Bromofuran can be converted into 3-furoic acid by reaction with butyl lithium to give 3-lithiofuran followed by reaction with carbon dioxide (Y. Fukuyama, et al., *Synthesis*, 443–444 (1974); I. Fleming, et al., *Synthesis*, 898 (1985)) or by electrocarboxylation (O. Sock, et al., *Tetrahedron Letters*, 26, 1509–1512 (1985)). These methods, however, are expensive and difficult to adapt to commercial scale operation. Additionally, 3-bromofuran is prohibitively expensive for use as a starting material.

Other processes for preparing 3-furoic acid and esters thereof include (1) the rhodium-catalyzed reaction of alkyl formyldiazoacetate with vinyl ethers (E. Wenkert, et al., *J. Organic Chem.*, 55, 4975–4976 (1990)); (2) Diels Alder reactions of oxazoles with propiolic acid or ester (S. R. Ohlsen, et al., *J. Chem. Soc.* (C), 1632–1633 (1971); G. Ya. Kondrat'eva, et al., *Proc. of the Academy of Sciences, USSR (Chem.)*, 200, 862–864 (1971)); and (3) oxidative addition of ethyl formylacetate with vinyl acetate (E. Baciocchi, et al., *Synthetic Communications*, 18, 1841–1846 (1988)). These processes suffer from the use of expensive and/or hazardous starting materials and low yields.

F. Effenberger, et al., *Chem. Ber.*, 115, 2766–2782 (1982) and M. Hojo, et al., *Synthesis*, 1016–1017 (1986) describe the trichloroacetylation and trifluoroacetylation of 2,3-dihydrofuran to produce 2,3-dihydro-4-trichloroacetylfuran and 2,3-dihydro-4-trifluoroacetylfuran in good yield. These trihalomethylketone intermediates can be hydrolyzed to yield 2,3-dihydro-4-furoic acid (M. Hojo, et al., *Synthesis*, 1016–1017 (1986); N. Zanatta, et al., *J. Heterocyclic Chem.*, 34, 509–513 (1997)). P. Maynard-Faure, et al., *Tetrahedron Letters*, 39, 2315–2318 (1998) have shown that the trichloromethylketone intermediates can be converted into their esters, i.e., alkyl 2,3-dihydro-4-furoates, by treatment with an alcohol and potassium carbonate.

Methyl 3-furoate has been produced in 18% yield by the bromination of methyl 2,3-dihydro-4-furoate with N-bromosuccinimide followed by heating with 50% aqueous potassium hydroxide (J. T. Wrobel, et al., *Rocz. Chem.*, 40, 1005–1018 (1966)). Methyl and ethyl 2,3-dihydro-4-furoate have been brominated with bromine to give methyl and ethyl 2,3-dibromo-tetrahydro-3-furoate (W. Hasenbrink, *Liebigs Ann. Chem.*, 468–476 (1974)). These dibromides can be dehydrobrominated to produce methyl and ethyl 3-furoate but the yield is low and side-products require separation.

BRIEF SUMMARY OF THE INVENTION

An efficient, two-step process for the preparation of alkyl 3-furoates from 4-acyl-2,3-dihydrofurans has been developed. The present invention provides a process for preparing a compound having the formula:

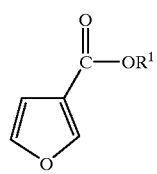

(I)

which comprises the steps of:
(1) contacting a compound having the formula:

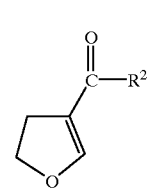

(II)

with a halogenating agent in the presence of an alkanol to obtain an intermediate compound having the formula:

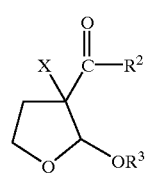

(III)

and
(2) contacting intermediate compound (III) with a strong base to produce compound (I) provided that step (2) is carried out in the presence of a source of alkoxide when $R^2$ is perhaloalkyl; wherein $R^1$ is alkyl; $R^2$ is perhaloalkyl or alkoxy; $R^3$ is alkyl; and X is halogen. The intermediate compounds of formula (III) are novel compositions of matter. If desired, 3-furoic acid can be obtained from ester (I) by hydrolysis. The alkyl 3-furoates obtained in accordance with the process of the present invention are useful for the production of pharmaceutical products (see for example the preparation of an anti-inflammatory agent by D. H. Williams and D. John Faulkner, *Tetrahedron*, 52, 4245–4256 (1996)). Ethyl 3-furoate has found utility as a marine and fresh water antifoulant in coating compositions (U.S. Pat. No. 5,259,701).

DETAILED DESCRIPTION

The starting material for the process of the present invention is a 4-acyl-2,3-dihydrofuran of formula (II). Compounds (II) wherein $R^2$ is a perhaloalkyl group can be prepared according to known procedures such as those described by F. Effenberger, et al., *Chem. Ber.*, 115, 2766–2782 (1982) and M. Hojo, et al., *Synthesis*, 1016–1017 (1986). The perhaloalkyl group may have up to about 4 carbon atoms and the halo substitutents may be selected from chloro, bromo, iodo and fluoro. The perhaloalkyl group which $R^2$ may represent most preferably is trichloromethyl. It may be possible to form the perhaloalkyl group during the first step of the process of my invention wherein the starting material is contacted with a halogenating agent. For example, 4-(dichloroacetyl)-2,3-dihydrofuran may be converted by a brominating agent to a 2-alkoxy-3-bromo-3-(bromo-dichloroacetyl) tetrahydrofuran intermediate compound.

The trihaloacetyl group (—C(O)CX$_3$) is useful in organic synthesis because it behaves much as an carboxylic acid chloride, i.e., it may be hydrolyzed to the carboxylic acid in what is known as the "haloform reaction" (R. C. Fuson, B. A. *Bull, Chem. Rev.*, 15, 275(1934)) or converted to an ester by base-catalyzed reaction with an alkanol. A trihalomethane (haloform) is the by-product of this reaction. Normally in the haloform reaction a methyl ketone is halogenated under basic conditions resulting in formation of an intermediate trihalomethyl ketone which hydrolyzes to a carboxylic acid and a trihalomethane. The hydrolysis reaction is known where the attached halogens are fluorine, chlorine, bromine and/or iodine. It is not necessary that all three halogens of the trihalomethyl ketone be the same. Perhaloalkanoyl groups containing more than 2 carbon atoms similarly are useful in the haloform reaction. A convenient and high yield process to prepare these starting materials is via the acylation of 2,3-dihydrofuran. For example, as already discussed, 2,3-dihydro-4-trichloroacetylfuran [Compound (II), $R^2$=CCl$_3$] is produced in high yield and selectivity by the reaction of trichloroacetyl chloride with 2,3-dihydrofuran in the presence of pyridine as an acid scavenger. The reaction also may be performed with trichloroacetic anhydride although trichloroacetyl chloride is preferred. Other acid scavengers may be employed, e.g., alkyl-substituted pyridines and trialkylamines, but pyridine is preferred. It is not necessary that all halogens of the perhaloalkanoyl group be the same. For example 2,3-dihydro-4-(bromodichloroacetyl)furan may be used as well. 2,3-Dihydro-4-trichloroacetylfuran is the preferred starting material of the process of this invention.

Alternatively, the corresponding ester [Compound (II), $R^2$=alkoxy] may be employed as the starting material. The alkoxy may have up to about 8 carbon atoms, preferably up to about 4 carbon atoms and preferably, the alkoxy group is methoxy or ethoxy. Such ester starting materials may be obtained from the analogous 2,3-dihydro-4-(perhaloalkanoyl)furans according to known procedures.

In the first step of the process of this invention, a compound having the formula:

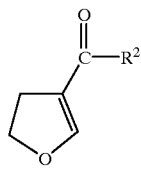

(II)

is contacted with a halogenating agent in the presence of an alkanol to obtain an intermediate compound having the formula:

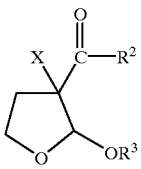

(III)

wherein $R^2$ is perhaloalkyl or alkoxy; $R^3$ is alkyl; and X is halogen. The halogenating agent may be a chlorinating agent or, preferably, a brominating agent. Examples of such halogenating agents include bromine, N-bromosuccinimide, 1,3-dibromo-5,5-dimethylhydantoin, chlorine, 1,3-dichloro-5,5-dimethylhydantoin and N-chlorosuccinimide. The amount of halogenating agent employed should be sufficient to convert essentially all of Compound (II) to Compound (III). Thus, at least one mole of bromine and N-bromosuccinimide and at least 0.5 mole of 1,3-dibromo-5,5-dimethylhydantoin normally is used per mole of Compound (II). A slight excess, e.g., up to about 10 mole percent excess, of the halogenating agent may be used. The halogenating agent preferably is a brominating agent, especially 1,3-dibromo-5,5-dimethylhydantoin. When bromine or chlorine is used as the halogenating agent, an acid scavenger is needed to consume by-product hydrogen bromide or hydrogen chloride. Examples of such acid scavengers include sodium bicarbonate and sodium carbonate.

In step (1), the halogenation is carried out in the presence of an alkanol which forms the alkoxy group represented by -OR$^3$. The alkanol (and the alkoxy group derived therefrom) may have up to about 8 carbon atoms but preferably is a primary alkanol have up to 4 carbon atoms and, most preferably, is methanol or ethanol. The amount of alkanol employed normally is at least one mole alkanol per mole of starting material (II) and may be in the range of about 1.1 to 10 moles per mole of starting material (II). An inert auxiliary solvent may be used, but is not required, in the halogenation of step (1). Examples of such inert solvents include aliphatic and aromatic hydrocarbons, e.g., hexane, heptane, decane, toluene and the isomers of xylene; and halogenated aliphatic and aromatic hydrocarbons such as 1,1,1-trichloroethane, perchloroethylene, chlorobenzene and the various isomers of dichlorobenzene. The optional hydrocarbon and halogenated hydrocarbon solvents preferably contain from 6 to 12 carbon atoms. The optional auxiliary solvent must also be inert to the strong base of step (2) if it is not removed first. The preferred mode is halogenate in an alkanol without an inert auxiliary solvent. Since water causes side reactions, step (1) normally is carried out under substantially anhydrous conditions.

Step (1) of my novel process may be carried out at temperatures in the range of about −20 to 60° C., preferably at temperatures in the range of about 0 to 20° C. Pressure is not an important feature of the present process and thus various total pressures, e.g., pressures moderately above or below ambient pressure, may be used.

The second step of the present process of this invention involves the base-mediated conversion of intermediate compound (III) to alkyl furoate (I). Step (2) includes contacting intermediate compound (III) with a strong base in the presence of a solvent. Examples of such strong bases include alkoxides of the alkali metals and strongly basic amines such as 1,8-diazabicyclo[5.4.0]undec-7-ene and 1,5-diazabicyclo[4.3.0]non-5-ene. The strong base preferably is an alkali metal alkoxides such as alkoxides having the formula M—O—$R^4$ wherein M is an alkali metal, preferably sodium or potassium, most preferably, sodium, and $R^4$ is an alkyl group have up to about 8 carbon atoms, preferably up to about 4 carbon atoms. The alkali alkoxide most preferably is sodium methoxide or ethoxide. The amount of bases used typically is at least 1 mole or equivalent, preferably 1.2 to 3 moles or equivalents, of base per mole of intermediate compound (III) present. If the process is carried out without isolating intermediate compound (III), the reaction mixture have intermediate compound (III) also normally contains residues of halogenating agents which react with and thus consume some base. Consequently, when the process is operated without isolating intermediate compound (III), e.g., in a single reactor, the amount of base preferably is about 2 to 4 moles or equivalents base per mole of intermediate compound (III) present.

The second step of my novel process is carried out in the presence of a solvent. Examples of the solvents which may be used in step (2) include the alkanols, the aliphatic and aromatic hydrocarbons and the halogenated aromatic hydrocarbons described above. When $R^2$ of intermediate Compound (III) is perhaloalkyl, step (2) is carried out in the presence of a alkoxy-providing compound which will effect conversion of the perhaloalkyl group to an alkoxy group. The alkoxy-providing compound may be an alkali metal alkoxide which is utilized as the bases in step (2). Alternatively, the alkoxy-providing compound may be an alkanol such as one of the alkanols which may be used in the first step of the process, i.e., an alkanol have up to about 8 carbon atoms, preferably a primary alkanol have up to 4 carbon atoms and, most preferably, methanol or ethanol. The alkyl group represented by R', therefore, may contain up to about 8 carbon atoms, preferably up to about 4 carbon atoms, most preferably methyl or ethyl.

Step (2) may be carried out at in the temperature in the range of about 25 to 100° C., preferably at temperatures in the range of about 50 to 80° C. As in the case of step (1), pressure is not an important feature of the second step of the present process and thus various total pressures, e.g., pressures moderately above or below ambient pressure, may be used, for example, to achieve a reaction temperature of the atmospheric boiling point of the reaction mixture. Also, as is the case for the first step, water cause side reactions, therefore step (2) is also normally carried out under substantially anhydrous conditions.

EXAMPLES

The operation of the process and preparation of the novel intermediate compounds provided by the present invention are further illustrated by the following examples.

Reference Example 1

Preparation of 2,3-Dihydro-4-Trichloroacetylfuran

To a nitrogen-purged, 5000-mL, three-neck, round-bottom flask equipped with a bottom stopcock, thermometer, mechanical stirrer, addition funnel and ice bath was charged 330.0 g (4.70 moles) of 2,3-dihydrofuran, 391 g (4.95 moles) of pyridine, and 1000 mL of n-heptane. The mixture was cooled to 10° C. then trichloroacetyl chloride (500 mL, 815 g, 4.48 moles) was added dropwise from the addition funnel. An ice bath was used to hold the reaction mixture at 11 to 220° C. during the 190 minute addition. The resulting yellow slurry was stirred at 22 to 28° C. for 45 minutes. To the mixture was added 700 mL of 10% aqueous HCl. After stirring to dissolve the solids, the lower (aqueous) layer was separated and discarded. The organic layer was washed sequentially with 500 mL of 10% HCl, 250 mL of 5% aqueous sodium bicarbonate and finally with 250 mL of water. The solution was placed in a 3000-mL, three-neck, round-bottom flask equipped with a magnetic stirrer, thermowell/thermocouple, heating mantle, and 12-inch Vigreux distillation head. The mixture was heated under vacuum (130 mm) to distill off the water/heptane azeotrope then most of the heptane. The mixture was distilled to a pot temperature of 102° C. (head temperature was 50° C.). A total of 1135 mL of distillate was collected. The resulting crude 2,3-dihydro-4-trichloroacetylfuran (881.38 g, theory 965.26 g) was 98.4% assay by nuclear magnetic resonance (NMR) (89.8% assay-yield). The crude product was used directly in the following example.

Example 1

Step (1) —Preparation of 3-Bromo-2-Methoxy-3Trichloroacetyltetrahydrofuran

To a nitrogen-purged, 2000-mL, four-neck, round-bottom flask equipped with a thermocouple/thermowell, ice bath, addition funnel, 15-inch Vigreux column, distillation head, and mechanical stirrer was charged 200 mL of methanol. The solvent was cooled to about 5° C. then 145.0 g (0.497 mole) of 98% 1,3-dibromo-5,5-dimethylhydantoin was added to the flask. The slurry was cooled to 0 to 5° C. then 219.0 g (1.00 mole) of 98.4% 2,3-dihydro-4-trichloroacetylfuran was added from the addition funnel over a period of about 30 minutes while holding the temperature at 0 to 60° C. with a Dry Ice/acetone bath. The bath then was removed and the mixture allowed to warm to 350C over about 30 minutes. Gas chromatography (GC) showed complete and selective conversion to 3-bromo-2-methoxy-3-trichloroacetyltetrahydrofuran. The identity of the product was confirmed by mass spectrometry. The next step was continued with this intermediate solution and equipment setup.

Step (2) —Preparation of Methyl 3-furoate

The final solution from the previous step was heated to about 35° C. then the addition of 640 mL (605 g, 2.80 moles) of 25% methanolic sodium methoxide from the addition funnel was begun. The exothermic reaction raised the pot temperature to about 70° C. and solvent began to distill (58 to 64° C head temperature). The addition was performed over about four hours while simultaneously stripping off solvent (chloroform and methanol). Fine solids began to form part-way through the addition. Thirty minutes after addition the reaction mixture was sampled to insure complete reaction (if incomplete, add more sodium methoxide).

GC of the reaction mixture showed complete conversion to methyl 3-furoate. Solvent stripping was continued to a pot temperature of 82° C. (head temperature 63° C.) to give a medium slurry (collected about 800 mL of distillate). To the slurry was added 250 mL of toluene from the addition funnel. Then 55 mL (58 g, 0.96 mole) of acetic acid was added from the addition funnel over about five minutes to neutralize excess sodium methoxide. A reaction slurry sample was taken and dissolved in water to check pH (in this experiment it was about 5 by pH paper). If the pH is not less than 7 then more acetic acid is needed. Solvent stripping was continued to a pot temperature of 11 50C and a head temperature of 70° C. or higher (indicating that most of the methanol was removed). The mixture was cooled to room temperature overnight then just enough water was added to dissolve the solids (400 mL). The lower (aqueous) layer was discarded and the organic layer was washed twice with 100 mL of 5% aqueous sodium bicarbonate and finally with 100 mL of saturated, aqueous sodium bicarbonate. The organic layer was filtered then distilled using a 10-inch Vigreux column at 200 mm. After removing solvent and low boilers, the product fraction was collected at 119 to 120° C. The yield of methyl 3-furoate was 90.1 g (71.4% of theoretical 126.11 g from 2,3-dihydro-4-trichloroacetylfuran) and GC analysis showed 99.7 area% purity. The identity of the product was confirmed by NMR and mass spectrometry.

Example 2

Step (1)—Preparation of Ethyl 3-bromo-2-ethoxytetrahydro-3-furoate

To a nitrogen-purged, 1000-mL, four-neck, round-bottom flask equipped with a thermocouple/thermowell, Dry Ice/acetone bath, addition funnel, condenser, and magnetic stirrer was charged 200 mL of ethanol, 142.12 g (1.00 mole) of ethyl 2,3-dihydro-4-furoate, and 93.0 g (1.11 mole) of sodium bicarbonate. The slurry was cooled to about 0° C. then 159.1 g (0.995 mole) of bromine was added dropwise from the addition funnel over 75 minutes at a temperature of -3 to 30° C. After 15 minutes the bath was removed and the light yellow slurry allowed to warm to room temperature over about two hours. The mixture was filtered and the solids rinsed with ethanol. Solvent was stripped from the filtrate by rotary evaporation at up to 45° C. (70 mm). To the concentrated product was added 100 mL of water. The layers were separated and the aqueous layer extracted with 50 mL of dichloromethane. The organic layers were combined and washed with 100 mL of water containing 0.23 g of sodium thiosulfate then with 100 mL of 5% aqueous sodium bicarbonate. The organic layer was dried with anhydrous magnesium sulfate, then filtered and concentrated by rotary evaporation at up to 45° C. (70 mm). The resulting crude product weighed 270.5 g and contained 5.4 weight percent dichloromethane by NMR (theory 267.12 g, 95.8% yield). A portion of this crude product (71.01 g) was distilled using a 10-inch Vigreux column at 3 mm. The product fraction was collected at 101 to 102° C. The yield of distilled ethyl 3-bromo-2-ethoxytetrahydro-3-furoate was 56.63 g (80.8%). The identity of the product was confirmed NMR and mass spectrometry.

$^1$H NMR (300 MHz, CDCl$_3$): δ6 1.14 (t, 3H), 1.31 (t, 3H), 2.36 (m, 1H), 2.97 (m, 1H), 3.53 (m, 1H), 3.74 (m, 1H), 4.24 (m, 4H), 5.24 (s, 1H). $^{13}$CNMR (75 MHz, CDCl$_3$): δ813.96, 15.02, 35.30, 61.98, 62.91, 63.91, 65.41, 66.65, 107.39, 167.44.

Step (2) —Preparation of Ethyl 3-furoate

To a nitrogen-purged, 300-mL, three-neck, round-bottom flask equipped with a thermocouple/thermowell, addition funnel, distillation head, and magnetic stirrer was charged 75 mL of toluene and 26.71 g (0.100 mole) of distilled ethyl 3-bromo-2-ethoxytetrahydro-3-furoate and 42 mL (0.11 mole) of 21 % alcoholic sodium ethoxide. The mixture was heated to 50° C. while following the course of reaction by GC. An additional 17 mL (0.046 mole) of sodium ethoxide solution was needed to complete the reaction. The pressure of the system was lowered to about 210 mm to distill the ethanol/toluene azeotrope. When most of the ethanol was removed the mixture was cooled to room temperature and 50 mL of 5% hydrochloric acid was added. The layers were separated and the aqueous layer was extracted once with 25 mL of toluene. The two organic layers were combined and washed with 50 mL of 5% aqueous sodium bicarbonate and 50 mL of saturated sodium bicarbonate. The solution was dried over anhydrous magnesium sulfate and decolorizing carbon then filtered. Solvent was removed from the filtrate by distillation through a 1 0-inch Vigreux column at atmospheric pressure. The resulting ethyl 3-furoate weighed 11.25 g. Analysis by GC showed 90.4 area% ethyl 3-furoate and 9.6 area% toluene. The assay-yield of ethyl 3-furoate was 10.2 g (72.6% of theory). The identity of the product was confirmed by NMR and mass spectrometry.

The invention has been described in detail with particular reference to preferred embodiments thereof, but it will be understood that variations and modifications can be effected within the spirit and scope of the invention.

I claim:

1. Process for preparing a compound having the formula:

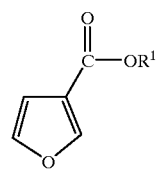

(I)

which comprises the steps of:
(1) contacting a compound having the formula:

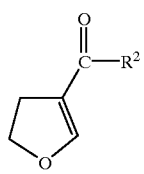

(II)

with a halogenating agent in the presence of an alkanol to obtain an intermediate compound having the formula:

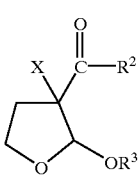

(III)

and
(2) contacting intermediate compound (III) with a strong base to produce compound (I) provided that step (2) is carried out in the presence of a source of alkoxide when R² is perhaloalkyl;

wherein R¹ is alkyl; R² is perhaloalkyl or alkoxy; R³ is alkyl; and X is halogen.

2. Process according to claim 1 wherein the halogenating agent is bromine, N-bromosuccinimide, 1,3-dibromo-5,5-dimethylhydantoin, chlorine, 1,3-dichloro-5,5-dimethylhydantoin and N-chlorosuccinimide, the alkanol is an alkanol having up to about 4 carbon atoms, the base is an alkali metal alkoxide, 1,8-diazabicyclo[5.4.0]undec-7-ene or 1,5-diazabi-cyclo[4.3.0]non-5-ene, R¹ is alkyl of up to about 4 carbon atoms; R²is perhalomethyl; R³ is alkyl of up to about 4 carbon atoms; X is chloro or bromo; provided that step (2) is carried out in the presence of an alkanol having up to about 4 carbon atoms when the base is 1,8-diazabicyclo[5.4.0]undec-7-ene or 1,5-diazabicyclo[4.3.0]non-5-ene.

3. Process according to claim 2 wherein the base is an alkali metal alkoxide having the formula M—O—R⁴ wherein M is an alkali metal and R⁴ is an alkyl group having up to about 4 carbon atoms; step (1) is carried out at a temperature of about −20 to 60° C.; and step (2) is carried out at a temperature of about 25 to 100° C.

4. Process according to claim 3 wherein the base is sodium methoxide or ethoxide.

5. Process according to claim 1 wherein the halogenating agent is bromine, N-bromosuccinimide, 1,3-dibromo-5,5-dimethylhydantoin, chlorine, 1,3-dichloro-5,5-dimethylhydantoin and N-chlorosuccinimide, the alkanol is an alkanol having up to about 4 carbon atoms, the base is an alkali metal alkoxide, R¹ is alkyl of up to about 4 carbon atoms; R² is alkoxy having up to about 4 carbon atoms; R³ is alkyl of up to about 4 carbon 30 atoms, chloro or bromo; and X is chloro or bromo.

6. Process according to claim 5 wherein the base is an alkali metal alkoxide having the formula M—O—R⁴ wherein M is an alkali metal and R⁴ is an alkyl group having up to about 4 carbon atoms; step (1) is carried out at a temperature of about −20 to 60° C.; and step (2) is carried out at a temperature of about 25 to 100° C.

7. Process according to claim 6 wherein the base is sodium methoxide or ethoxide.

8. Process for preparing a compound having the formula:

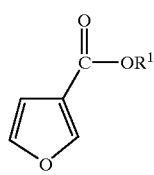

(I)

which comprises the steps of:

(1) contacting a compound having the formula:

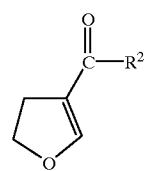

(II)

with a halogenating agent selected from bromine, N-bromosuccinimide, 1,3-dibromo-5,5-dimethylhydantoin, chlorine, 1,3-dichloro-5,5-dimethyl-hydantoin and N-chlorosuccinimide in the presence of an alkanol having up to about 4 carbon atoms to obtain an intermediate compound having the formula:

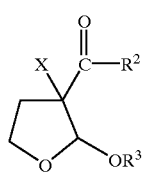

(III)

and
(2) contacting intermediate compound (III) with a sodium or potassium alkoxide having up to about 4 carbon atoms to produce compound (I); wherein R¹ is alkyl of up to about 4 carbon atoms; R² is perhalomethyl; R³ is alkyl having up to about 4 carbon atoms; and X is chloro or bromo.

9. Process according to claim 8 wherein the halogenating agent is 1,3-dibromo-5,5-dimethylhydantoin, the alkanol is methanol or ethanol, R¹ is methyl or ethyl; R² is trichloromethyl; R³ is methyl or ethyl, and X is bromo.

10. A compound having the formula:

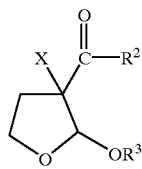

(III)

wherein R² is perhaloalkyl or alkoxy; R³ is alkyl; and X is halogen.

11. A compound according to claim 10 wherein R² is perhalomethyl or alkoxy having up to about 4 carbon atoms; R³ is alkyl of up to about 4 carbon atoms; and X is chloro or bromo.

12. A compound according to claim 10 wherein R² is trichloromethyl; R³ is methyl or ethyl; and X is bromo.

13. A compound according to claim 10 wherein R² is methoxy or ethoxy; R³ is methyl or ethyl; and X is bromo.

* * * * *